Figure 1:
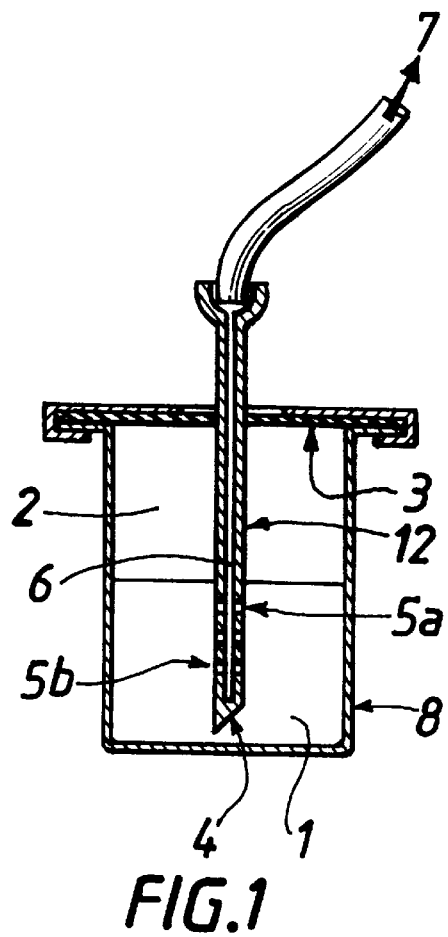

United States Patent
Vial et al.

[11] Patent Number: 5,938,939
[45] Date of Patent: Aug. 17, 1999

[54] SUCTION DEVICE ENABLING FINE SOLID PARTICLES TO BE SEPARATED FROM A LIQUID

[75] Inventors: Jean Vial, Dardilly; Jean-Yves Ortholand; Marcel Calleja, both of Lyons, all of France

[73] Assignee: Rhone-Poulenc Agrochimie, Lyons, France

[21] Appl. No.: 08/772,564

[22] Filed: Dec. 26, 1996

[30] Foreign Application Priority Data

Dec. 29, 1995 [FR] France .................................. 95 15877

[51] Int. Cl.$^6$ ............................. B01D 37/00; B01D 35/02
[52] U.S. Cl. .............................. 210/767; 422/62; 422/63; 422/101; 422/102; 436/177; 436/180; 73/863.23; 73/863.81
[58] Field of Search ........................... 210/767, 808; 422/99, 62, 101, 63, 102; 436/178, 177, 807, 180; 73/863.23, 863.81

[56] References Cited

U.S. PATENT DOCUMENTS 5,429,803   7/1995   Guirguis .
5,432,098   7/1995   Wilks .

FOREIGN PATENT DOCUMENTS 465 691   1/1992   European Pat. Off. .
59-48499  3/1984   Japan .

*Primary Examiner*—Robert J. Popovics
*Attorney, Agent, or Firm*—Scully, Scott, Murphy & Presser

[57] ABSTRACT

Device for separating the liquid and solid constituents of a chemical reaction mixture (1), comprising a metal filtering needle (12) provided with lateral holes (5) and able to pass through polymeric- or rubber-type membranes (3) without the latter losing their gastightness (2), a suction source (7) capable of sucking out a liquid from a closed vessel (8), a liquid evacuation channel (6) and an end-piece (4).

29 Claims, 1 Drawing Sheet

SUCTION DEVICE ENABLING FINE SOLID PARTICLES TO BE SEPARATED FROM A LIQUID

The subject of the present invention is a process and an apparatus for the implementation of processes for the preparation of chemicals and capable of operating in an automatic manner.

The synthesis of chemicals in an automatic manner is continuing to grow for all kinds of reasons, especially because of the need to increase safety and because of the multiplication of repetitive tasks.

Moreover, the synthesis of increasingly complicated products involving a large number of reaction steps requires an excessive amount of labour which it is desired to reduce by changing the method of synthesis. Furthermore, it is increasingly desired to manufacture a very large number of chemicals so as to be able to have materials with the most diverse properties.

These methods for the preparation of chemicals by automatic means often comprise a step of attaching certain reactants on a solid support, generally a polymeric support (also called resin), and then, after having carried out the reactions on the said solid supports in a suitable manner, it is necessary to separate the solid support from the participants of the reaction, this solid support itself being attached either to reactants or to reaction products.

Participants in a chemical reaction are understood to mean not only the reactants but also the reaction products and the other chemicals involved in the reaction, such as solvents, cosolvents, catalysts, cocatalysts, emulsifiers, dispersing agents, anti-foaming agents, additives, etc.

This separation from a solid reaction support causes various practical problems, these problems being all the more pronounced when automatic synthesis reactions are not completed in a single reaction but generally comprise a series of reactions. Each of these reactions involves very varied reaction participants and it is desirable that the separations be made as well as possible, failing which the mixtures become increasingly complex and secondary or parasitic reactions multiply and the products obtained are increasingly impure.

An additional difficulty in carrying out these reactions is associated with the fact that such reactions often take place in a particular atmosphere, for example in an inert atmosphere, and that it is difficult to carry out the desired separation without modifying the atmosphere or without causing it to lose its special properties.

One object of the present invention is therefore to provide means of separation from the solid reaction supports solving the practical problems which arise and which have been described hereinabove.

Another object of the present invention is to provide means of separation from the solid reaction supports enabling automatic and sequenced chemical reactions to be carried out with simple and convenient separation from the solid reaction supports.

Another object of the present invention is to allow the sequence of successive chemical reactions without an excess of reactant involved in one of the steps impairing a subsequent step.

Another object of the present invention is also to allow the sequence of successive chemical reactions and the removal of the excesses of reactants employed in a previous reaction.

Another object of the present invention is to provide means of separation from the solid reaction supports enabling automatic chemical reactions to be carried out while disturbing to the minimum the atmosphere prevailing above the reaction mixture.

It has now been discovered that these objects could be achieved by virtue of the device according to the present invention as well as by virtue of the process for the preparation of chemicals according to the present invention.

The invention therefore relates to a process of separating a solid participant in a chemical reaction mixture comprising solid particles and a liquid, these being in a closed reaction vessel, the said solid participant in the said chemical reaction mixture being a support chemically bound to a reactant or reaction product, the said process comprising the step of sucking the liquid phase from the said reaction mixture using suction means, the suction taking place without substantial disturbance of the atmosphere in the said vessel, the said suction means being capable of passing through a wall of the said vessel without substantially modifying the gas exchanges between the inside and outside of the said vessel, and the said suction means being capable of penetrating into the said vessel and of being withdrawn therefrom without the latter losing its gastightness when the said suction means are withdrawn from the said vessel, the said suction means comprising means of perforating said wall without the latter losing its gastightness, the said suction means furthermore comprising means of conveying the liquid sucked out of the said vessel to the outside, these liquid conveying means not being capable of conveying the solid particles present in the said vessel, the said suction means furthermore comprising means enabling fine solid particles to be separated from a liquid without giving rise to a blocking phenomenon.

In the foregoing, as well as in what follows, a certain change in pressure of the atmosphere in the vessel may nevertheless take place because of the disappearance of liquid from the vessel by suction; however, there is no change in the nature or the substance of the said atmosphere because of the absence of gas exchange with the outside during suction.

The perforation means which may be employed in the invention are, according to another aspect, cutting means or piercing means.

The invention furthermore relates to a (more general) process for the preparation of chemicals in an automated and/or programmed manner, the said process comprising several sequenced or successive chemical reactions. In addition, this process is particularly advantageous when it comprises a phase of removal of excess reactant(s) present on completion of a reaction step by suction before the next reaction step.

Moreover, the present invention also relates to a suction means enabling a liquid to be sucked out of a closed vessel, the said suction means being capable of passing through a wall of the said vessel without substantially modifying the gas exchanges between the inside and outside of the said vessel, and the said suction means being capable of penetrating into the said vessel and of being withdrawn therefrom without the latter losing its gastightness when the said suction means are withdrawn from the said vessel, and the said suction means comprising means of perforating said wall without the latter losing its gastightness, and the said suction means furthermore comprising means of conveying the liquid sucked out of the said vessel to the outside, these liquid conveying means not being capable of conveying the solid particles present in the said vessel, and the said suction means furthermore comprising means enabling fine solid particles to be separated from a liquid without giving rise to a blocking phenomenon.

Moreover, the present invention also relates to an apparatus for carrying out chemical reactions comprising a closed reaction vessel, as well as means of sucking liquid out of the said vessel, the said suction means being capable of passing through a wall of the said vessel without substantially modifying the gas exchanges between the inside and outside of the said vessel, and the said suction means being capable of penetrating into the said vessel and of being withdrawn therefrom without the latter losing its gastightness when the said suction means are withdrawn from the said vessel, and the said suction means comprising means of perforating said wall without the latter losing its gastightness, and the said suction means furthermore comprising means of conveying the liquid sucked out of the said vessel to the outside, these liquid conveying means not being capable of conveying the solid particles present in the said vessel, and the said suction means furthermore comprising means enabling fine solid particles to be separated from a liquid without giving rise to a blocking phenomenon.

The invention furthermore relates to an apparatus as described previously and in addition comprising a robotized and programmable part enabling sequenced or successive chemical reactions to be carried out.

Preferably, the suction means employed in the invention comprise:

a suction source capable of sucking out a liquid, means of conveying the liquid, principally comprising a channel for evacuating the liquid, together with the walls of this channel, an end-piece at one of the ends of this channel, this end-piece comprising, on the one hand, cutting means enabling it to pass through polymeric- or rubber-type membranes and, on the other hand, filtration means capable of separating solid particles from a liquid.

In an even more preferred manner, the said suction means are such that their evacuation channel and the cutting means and the end-piece are all made from non-oxidizable metal, advantageously from the same metal, and/or from a single metal piece.

In order to be suitable for the process according to the invention in an effective manner, the said suction means have an end-piece with filtration means capable of distinguishing between the liquid and solid particles having a diameter of between 25 microns and 1 mm; preferably, the said filtration means are capable of distinguishing between the liquid and solid particles having a diameter of between 50 and 300 microns.

By way of non-limiting illustration, the resin which is to be filtered may be of the Wang or Merrifield type or of any other type known per se. The most common resins are polystyrene resins, the polystyrene being crosslinked by, for example, divinylbenzene, with attachment of suitable reactive chemical groups, such as hydroxyl or amino groups or another group. These techniques are well known to those skilled in the art.

These filtration means are preferably capable of not being blocked by the solid particles. This may be achieved by the fact that they comprise, on the one and, a wall closing off the liquid evacuation channel o that the latter does not have direct access to the liquid phase in the closed vessel and, on the other hand, a plurality of fine interstices advantageously arranged laterally with respect to the evacuation channel.

According to a variant of the invention, this plurality of fine interstices consists of a multitude (several tens) of small bores having a diameter of less than 50 microns, or better still less than 25 microns. Advantageously, these holes are arranged radially from the centre of the evacuation channel towards the outside of this channel.

According to another variant of the invention, this plurality of fine interstices consists of a plurality of slots (generally arranged along the length of the liquid evacuation channel, that is to say parallel to the direction of this length) having a width of less than 50 microns, or better still less than 25 microns, the length of the said slots being generally greater than 1 mm and/or less than 10 mm.

According to yet another variant of the invention, the slots may be straight, or in the form of a cross, or having a curved shape or a right-angled shape. Although the slots are, along their major axis, preferably oriented parallel to the length of the filtering needle, it is nevertheless possible to choose other orientations, such as oblique slots or other orientations.

According to another variant of the invention, the filtration means are formed by a porous end-piece which is fixed (generally welded) to the evacuation channel, the pores in this porous end-piece corresponding to interstices having a diameter of less than 50 microns, or better still less than 25 microns.

According to the aspect of the invention relating to an apparatus for carrying out chemical reactions comprising a closed reaction vessel, as well as means of sucking liquid out of the said vessel, the said vessel generally comprises, by way of wall capable of being perforated by the suction means, a wall or cover made of polymeric or rubber material. Such a wall may consist of a disc and is sometimes designated by the term septum.

A more particular description of a particular embodiment of the device and of the apparatus according to the invention are given in FIG. 1.

This figure shows a closed vessel (8) provided with a perforable wall or septum (3). This vessel contains an atmosphere (2) and a liquid phase (1) in which resin particles having a size of between 50 and 100 microns are in suspension. The suction means comprise a suction source (7), a liquid evacuation channel (6) and the filtration means. The filtration means are preferably formed in the lateral wall of the needle, and the needle is then closed-off by the wall (4) closing off the channel (6). The filtration means then use a multitude (more than 50) of lateral perforations (5a) and (5b) each having a cross-sectional size of less than 25 microns. The evacuation channel (6), together with its closing-off wall (4), is in the form of a needle (12) having an internal diameter of between 0.1 mm and 3 mm. This needle (12) and the channel (6) form part of the liquid conveying means.

The implementation of the process according to the invention comprises the implementation of a chemical reaction in the vessel (8) followed by passing the needle (12) through the wall (3) until it reaches the liquid (1) [this does not disturb the atmosphere (2)]. Suction of the liquid then takes place due to the effect of the suction source (7) sucking through the channel (6) and the filtration means (5). After withdrawing the needle (12) from the vessel, there remains at the bottom of the vessel the solid not sucked out and, above it, the remaining atmosphere (2) (this remaining atmosphere not, in fact, having undergone gas exchanges with the outside).

Figures 2, 3A:
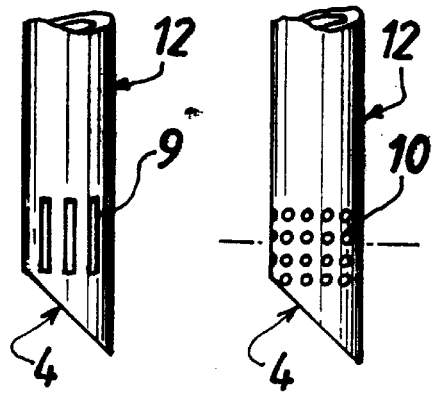

A variant of the suction means is described in FIG. 2 in which it may be seen that the filtration means comprise a plurality of slots (9) in addition to the closing-off wall (4). According to one non-limiting embodiment example, these slots have a width of 30 microns and a length of 2 mm.

Figure 3B:
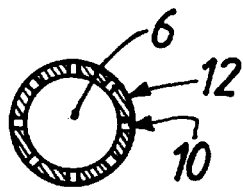

A variant of the suction means is described in FIG. 3*a* in which it may be seen that the filtration means comprise a plurality of holes (10) in addition to the closing-off wall (4). These holes may either be produced directly through the thickness of the walls of the needle (12) or else on an extension welded to the body of this needle. According to a non-limiting embodiment example, these holes have a diameter of 30 microns while the diameter of the filtering needle (12) is 2 mm. FIG. 3*b* illustrates a cross-section of the needle (12), showing the evacuation channel (6) inside the needle (12) and the radial arrangement of the holes (10).

The width of the slots in the examples of FIGS. 1 to 3 has been indicated as being, in a non-limiting manner, equal to 25 or 30 microns. From a general standpoint, as has already been stated, this width is less than 50 microns and preferably less than 25 microns.

Figure 4:
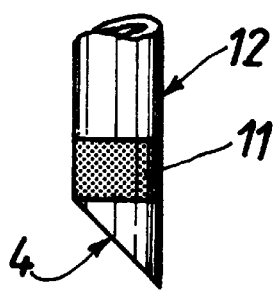

A variant of the suction means is described in FIG. 4 in which it may be seen that the filtration means comprise a porous end-piece (11) (with lateral porosity) welded to the evacuation channel, in addition to the closing-off wall (4).

The process according to the invention is advantageously implemented using the device according to the invention and it consists in separating a solid participant in a chemical reaction mixture comprising solid particles and a liquid, these being in a closed reaction vessel (2), the said solid participant in the said chemical reaction mixture being a support chemically bound to a reactant or reaction product, and the said process comprising a step of suction of the liquid phase from the said reaction mixture using suction means, suction taking place without substantially disturbing the atmosphere in the said vessel.

Figure 5A:
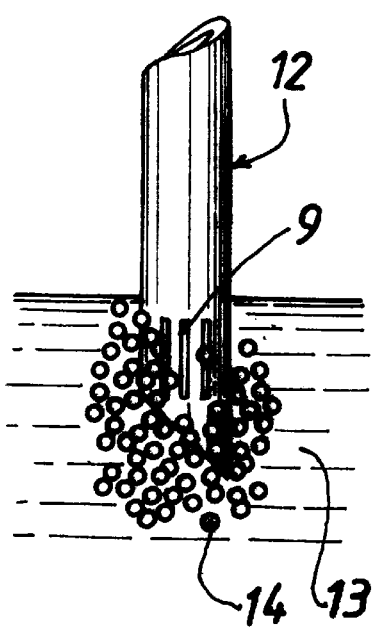

FIG. 5*a* illustrates a needle (12) with slots (9) dipped into a reaction mixture comprising a solvent (13) and a resin (14). The solvent may comprise reactants or certain soluble reaction products. The resin (14) may comprise a reaction product attached to the said resin. By way of non-limiting illustration, the resin may be a polyhydroxylated insoluble crosslinked polymer which has reacted completely or partly with an ester by a transesterification reaction, producing a resin comprising a plurality of ester groups attached to it. The resin is therefore the solid participant in the chemical reaction mixture.

Figure 5B:
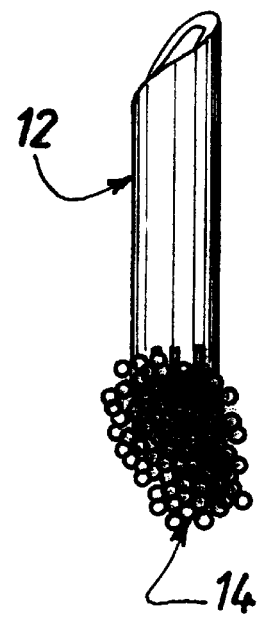

FIG. 5*b* illustrates the condition after applying the process according to the invention, that is to say during the separation by suction according to the process of the invention, while FIG. 5*a* illustrates the condition before separation by suction. In this FIG. 5*b*, the solvent (13) has disappeared and the resin (14) is still held by suction against the slots (9) or holes (10) of the needle (12).

We claim:

1. In a suction device(4, 5, 6, 7, 12) for enabling a liquid from a chemical reaction mixture which contains solid particles to be sucked out of a closed vessel (8), said suction device being passed through a wall (3) of said vessel in the absence of substantially any gas exchanges between the interior and the exterior of said vessel, said suction device penetrating into the interior of said vessel and being withdrawable therefrom without the vessel losing its gas tightness upon said suction device being withdrawn from said vessel, said suction device comprising vessel wall piercing means (12) including a liquid evacuation channel (6) and at a leading end thereof having means for perforating said vessel wall while the vessel maintains the gas tightness thereof, the improvement comprising:

said suction device including filtration means (5*a*, 5*b*, 6, 9, 10, 11) in fluid communication with said channel for conveying the liquid sucked out of said vessel to the exterior of said vessel, said liquid conveying means being incapable of conveying any solid particles present in said vessel, and said suction device filtration means (9, 10, 11) being dimensioned to separate the solid particles each having a diameter of between about 25 microns and 1 mm from the liquid (1) in said vessel and to retain said solid particles in said vessel without causing a blocking phenomenon at said filtration means.

2. Device according to claim 1, comprising:

a suction source (7) for sucking out a liquid from said vessel, said liquid evacuation channel (6) being closed off by an end-piece (4) located at one end of said channel, said end-piece (4) comprising means (12) for selectively cutting, perforating or piercing to facilitate passage through said wall (3) consisting of polymeric or rubber membranes, and said filtration means (5*a*, 5*b*, 9, 10, 11) separating solid particles from said liquid.

3. Device according to claim 2, wherein the liquid evacuation channel (6), the means for selectively cutting, perforating or piercing (12) and the end-piece (4) are each constituted of a non-oxidizable metal.

4. Device according to claim 3, wherein said components comprise a single metal piece.

5. Device according to claim 1, comprising suction source means (7) having an end-piece (4) with said filtration means adapted to effect said separation between said liquid and said solid particles.

6. Device according to claim 5, wherein said solid particles each have a diameter within the range of about 50 to 300 microns.

7. Device according to claim 1, wherein the filtration means comprises a further wall (4) closing off an end of the liquid evacuation channel (6) to prevent the liquid evacuation channel from having direct access to the liquid phase in the closed vessel (8), and a plurality of fine interstices arranged in said suction device so as to extend laterally for placing the liquid evacuation channel (6) in fluid communication with the liquid phase in said vessel (8).

8. Device according to claim 7, wherein the plurality of fine interstices consists of a multitude of small bores each having a diameter of less than 50 microns.

9. Device according to claim 8, wherein each said bore has a diameter of less than 25 microns.

10. Device according to claim 8, wherein the bores extend radially outwardly from the center of the evacuation channel.

11. Device according to claim 7, wherein the plurality of fine interstices consists of a plurality of slots each having a width of less than 50 microns.

12. Device according to claim 11, wherein each said slot has a width of less than 25 microns.

13. Device according to claim 12, wherein the length of each of the slots is within the range of about 1 mm to 10 mm.

14. Device according to claim 1, wherein the filtration means are formed by a porous end-piece (11) which is in fluid communication with the liquid evacuation channel (6) and attached to the wall piercing means (12), the pores in said porous end-piece comprising interstices each having a diameter of less than 50 microns.

15. Apparatus for carrying out chemical reactions, comprising a closed reaction vessel and a device according to claim 1.

16. Apparatus according to claim 15, wherein the closed reaction vessel comprises a wall capable of being perforated by the suction means, including a wall, cover or septum selectively made of a polymeric or rubber material.

17. Apparatus according to claim 15, comprising programmable means enabling the implementing of sequenced or successive chemical reactions.

18. A process for enabling a liquid from a chemical reaction mixture which contains solid particles to be sucked out of a closed vessel, said method comprising:

passing a suction device through a wall of said vessel in the absence of substantially any gas exchanges between the interior and the exterior of said vessel, causing said suction device to penetrate into the interior of said vessel and being withdrawable therefrom without the vessel losing its gas tightness upon said suction device being withdrawn from said vessel, having vessel wall piercing means of said suction device at a leading end thereof perforating said vessel wall while the vessel maintains a gas tightness, conveying the liquid sucked out of the said vessel to the exterior of said vessel, said conveyed liquid being incapable of entraining any solid particles present in said vessel, and retaining solid particles each having a diameter of between about 25 microns and 1 mm separated from the liquid in said vessel without causing a blocking phenomenon during liquid suctioning.

19. A process according to claim 18, comprising:

causing a suction source to suck out liquid from said vessel through a liquid evacuation channel, an end-piece located at one end of said channel, said end-piece (4) selectively facilitating cutting, perforating or piercing to facilitate passage through said wall consisting of polymeric or rubber membranes, and effecting filtration for separating said solid particles from said liquid.

20. A process according to claim 19, wherein the filtration is effected by a wall closing off the liquid evacuation channel to prevent the liquid evacuation channel from having direct access to the liquid phase in the closed vessel, and a plurality of fine interstices being arranged in said wall so as to extend laterally therethrough.

21. A process according to claim 20, wherein the plurality of fine interstices consists of a multitude of small bores each having a diameter of less than 50 microns.

22. A process according to claim 21, wherein each said bore has a diameter of less than 25 microns.

23. A process according to claim 21, wherein the bores extend radially outwardly from the center of the evacuation channel.

24. A process according to claim 20, wherein the plurality of fine interstices consists of a plurality of slots each having a width of less than 50 microns.

25. A process according to claim 24, wherein each said slot has a width of less than 25 microns.

26. A process according to claim 25, wherein the length of each of the slots is within the range of about 1 mm to 10 mm.

27. A process according to claim 19, wherein the filtration is effected by a porous end-piece which is fixed to the evacuation channel, the pores in said porous end-piece corresponding to interstices each having a diameter of less than 50 microns.

28. A process according to claim 18, wherein said solid particles each have a diameter within the range of about 50 to 300 microns.

29. A process according to claim 18, wherein said process is programmable to enable the implementing of sequenced or successive chemical reactions.

* * * * *